US011737737B2

(12) United States Patent
Fisher et al.

(10) Patent No.: US 11,737,737 B2
(45) Date of Patent: Aug. 29, 2023

(54) TELESCOPING NEEDLE ASSEMBLY WITH ROTATING NEEDLE

(71) Applicant: Praxis Holding LLC, Tampa, FL (US)

(72) Inventors: John Steele Fisher, Belleair, FL (US); Wayne A. Noda, Mission Viejo, CA (US); Nathaniel H. Pariseau, Tampa, FL (US); Andrew D. Palmer, Winter Springs, FL (US); Victor M. De Marco, Orlando, FL (US); Elizabeth A. Fisher, Tampa, FL (US); Christopher M. Drake, Portsmouth, NH (US)

(73) Assignee: Praxis Holding LLC, Tampa, FL (US)

( * ) Notice: Subject to any disclaimer, the term of this patent is extended or adjusted under 35 U.S.C. 154(b) by 3 days.

(21) Appl. No.: 17/241,327

(22) Filed: Apr. 27, 2021

(65) Prior Publication Data

US 2021/0244389 A1 Aug. 12, 2021

Related U.S. Application Data

(63) Continuation of application No. 17/066,031, filed on Oct. 8, 2020.

(60) Provisional application No. 62/913,015, filed on Oct. 9, 2019.

(51) Int. Cl.
| | |
|---|---|
| *A61B 10/02* | (2006.01) |
| *A61B 8/12* | (2006.01) |
| *A61B 17/34* | (2006.01) |
| *A61B 1/018* | (2006.01) |
| *A61B 17/00* | (2006.01) |
| *A61B 10/04* | (2006.01) |

(52) U.S. Cl.
CPC ............ *A61B 10/0266* (2013.01); *A61B 8/12* (2013.01); *A61B 17/3476* (2013.01); *A61B 1/018* (2013.01); *A61B 2010/0208* (2013.01); *A61B 2010/045* (2013.01); *A61B 2017/00991* (2013.01); *A61B 2017/3413* (2013.01)

(58) Field of Classification Search
None
See application file for complete search history.

(56) References Cited

U.S. PATENT DOCUMENTS

| | | | |
|---|---|---|---|
| 4,381,777 A | 5/1983 | Gamier | |
| 5,151,089 A | 9/1992 | Kirk, III et al. | |
| 6,402,701 B1 * | 6/2002 | Kaplan | ............... A61B 10/0233 600/567 |
| 6,689,072 B2 * | 2/2004 | Kaplan | ............... A61B 10/0233 600/564 |
| 2003/0195436 A1 * | 10/2003 | Van Bladel | ............. H04L 47/14 600/584 |
| 2006/0116605 A1 * | 6/2006 | Nakao | ................ A61B 10/0266 600/566 |

(Continued)

OTHER PUBLICATIONS

International Search Report for PCT/US20/54982 filed on Oct. 9, 2020, dated Feb. 17, 2021.

*Primary Examiner* — Benjamin S Melhus
(74) *Attorney, Agent, or Firm* — Nicholas Pfeifer; Smith & Hopen, P. A.

(57) ABSTRACT

A telescoping assembly such as an endobronchial ultrasound needle (EBUS) assembly includes a motor coupled to a biopsy needle within a telescoping housing to rotate (such as to oscillate) the needle during tissue harvest to improve harvesting.

16 Claims, 11 Drawing Sheets

(56) References Cited

U.S. PATENT DOCUMENTS

| | | | |
|---|---|---|---|
| 2009/0118641 A1* | 5/2009 | Van Dam | A61B 10/0266 |
| | | | 600/567 |
| 2009/0326412 A1 | 12/2009 | Pakter | |
| 2010/0121218 A1* | 5/2010 | Mugan | A61B 10/04 |
| | | | 600/567 |
| 2012/0116248 A1* | 5/2012 | McWeeney | A61B 10/0283 |
| | | | 600/567 |
| 2012/0226101 A1* | 9/2012 | Tinkham | A61B 1/00066 |
| | | | 600/106 |
| 2014/0088456 A1* | 3/2014 | Wang | A61B 10/04 |
| | | | 600/567 |
| 2016/0206294 A1* | 7/2016 | McWeeney | A61B 10/0283 |
| 2018/0008127 A1* | 1/2018 | Tinkham | A61B 1/00128 |
| 2019/0298898 A1* | 10/2019 | Stender | A61B 10/0283 |
| 2019/0307436 A1* | 10/2019 | Fisher | A61B 10/0283 |
| 2020/0246045 A1* | 8/2020 | Nakao | A61B 1/00133 |
| 2021/0038202 A1 | 2/2021 | Klein et al. | |
| 2022/0087661 A1* | 3/2022 | Fisher | A61B 10/0283 |
| 2022/0096065 A1* | 3/2022 | Fisher | A61B 17/3476 |

* cited by examiner

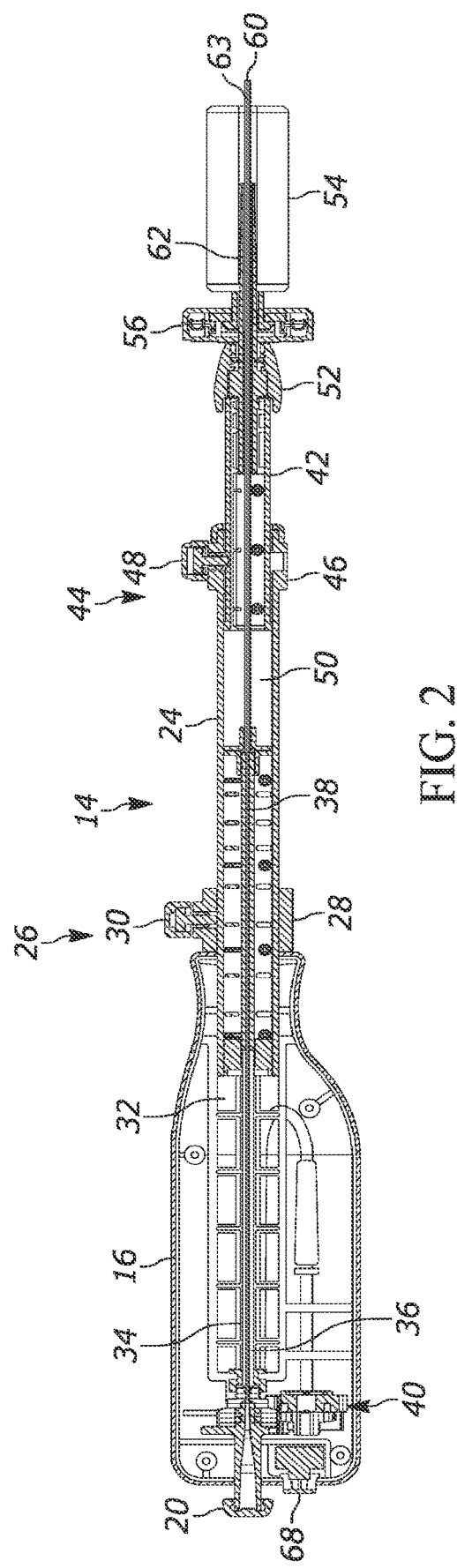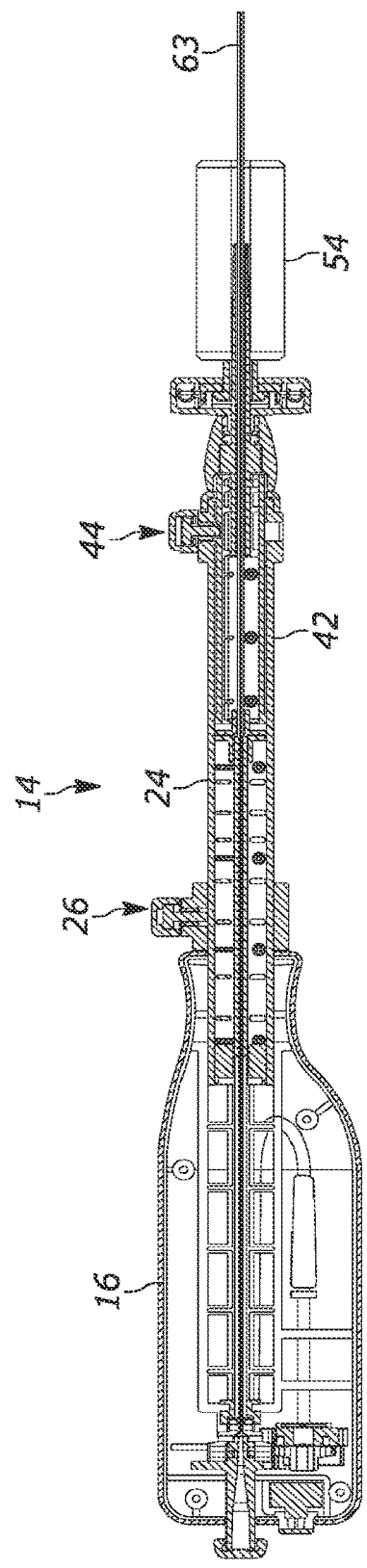
FIG. 2
FIG. 3

TELESCOPING NEEDLE ASSEMBLY WITH ROTATING NEEDLE

CROSS-REFERENCE TO RELATED APPLICATIONS

This nonprovisional application is a continuation of and claims priority to nonprovisional application Ser. No. 17/066,031, entitled TELESCOPING NEEDLE ASSEMBLY WITH ROTATING NEEDLE, filed Oct. 8, 2020 by the same inventor(s), which claims priority to provisional application No. 62/913,015, entitled "TELESCOPING NEEDLE ASSEMBLY WITH ROTATING NEEDLE," filed Oct. 9, 2019 by the same inventor(s).

BACKGROUND OF THE INVENTION

1. Field of the Invention

The application relates generally to syringe systems, and more particularly to biopsy syringe systems with rotating needles.

2. Brief Description of the Prior Art

It may be necessary to extract tissue from a patient for analysis to support diagnosis. For example, it may be necessary to extract tissue for "cytological" or cell harvest, as well as cores of tissue for breast biopsies, to ascertain the existence of disorders of the tissue.

Tissue extraction may be done by inserting a needle into the patient to withdraw tissue into a syringe connected to the needle, which is then used for dispensing the tissue onto analysis equipment.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

In the present assignee's co-pending U.S. Pat. No. 10,765,411 and U.S. patent application Ser. No. 16/013,522, both incorporated herein by reference, motorized tissue extraction devices are disclosed that conveniently avoid multiple needle insertions in the patient to obtain sufficient tissue for analysis while harvesting sufficient tissue for analysis.

Present principles are directed to extending techniques described in the referenced patent documents to telescoping assemblies such as endobronchial ultrasound needle (EBUS) applications, which are used to obtain tissue samples of lymph nodes in the lung.

Accordingly, an endobronchial ultrasound needle (EBUS) assembly includes a housing with at least first and second segments coupled telescopically. The EBUS assembly includes at least one hollow needle supported by the housing, and at least one motor in the housing and geared to the needle to cause the needle to rotate.

In example embodiments a sheath surrounds the needle and can move axially with the needle, while a stylet may extend through the needle prior to tissue harvesting to impede epithelial tissue from entering the needle prior to biopsy of tumor tissue.

In some embodiments the housing has at least three segments coupled telescopically.

In example implementations a power supply in the housing is connected to the motor to energize the motor. In such implementations a manipulable actuator may be provided on the housing to energize the motor.

In some examples a first manipulable mechanical stop is on the housing and is movable from a first position, in which the first and second segments can telescope relative to each other, and a second position, in which the first and second segments cannot telescope relative to each other. The first manipulable mechanical stop may include a thumb screw. A second manipulable mechanical stop may be on the housing and may be movable to lock second and third telescoping segments together.

In another aspect, a telescoping assembly includes a housing with at least first and second segments coupled telescopically. At least one hollow needle is supported by the housing, and at least one motor in the housing has an output shaft geared to the needle. At least one control circuit energizes the motor to cause the output shaft of the motor to rotate, such as to oscillate.

In another aspect, a method includes advancing a needle supported by a telescoping housing into a working channel of an endoscope while the endoscope is not inside a patient. The method includes telescoping the housing to a first configuration until the needle protrudes from a distal end of the working channel, locking the housing in the first configuration, and removing the needle from the endoscope. The method then includes advancing the endoscope into an object to image a constituent of the object to be sampled. With the housing in the first configuration, the needle is advanced into the working channel until the needle protrudes from the distal end of the working channel. The method includes manipulating the housing to telescope the housing to urge the needle into the constituent of the object to be sampled, actuating a motor in the housing to rotate the needle, and engaging a syringe with a proximal part of the housing to withdraw from the needle harvested constituent for analysis.

The invention accordingly comprises the features of construction, combination of elements, and arrangement of parts that will be exemplified in the disclosure set forth hereinafter and the scope of the invention will be indicated in the claims.

The details of the present application, both as to its structure and operation, can best be understood in reference to the accompanying drawings, in which like reference numerals refer to like parts.

BRIEF DESCRIPTION OF THE DRAWINGS

For a fuller understanding of the invention, reference should be made to the following detailed description, taken in connection with the accompanying drawings, in which:

FIG. 2 is a side cut-away view of the assembly shown in FIG. 1 in an initial configuration outside the patient;

FIGS. 3 and 4 are a side cut-away views of the assembly shown in FIG. 1 in a configuration outside the patient in which the assembly is adjusted telescopically to establish a length of protrusion of the needle distally beyond the endoscope;

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The phrases "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

It is to be understood that principles of constructions and operation set forth in the above-incorporated U.S. patent documents apply to the disclosure herein in relevant part taking account of the features set forth herein.

Figure 1:
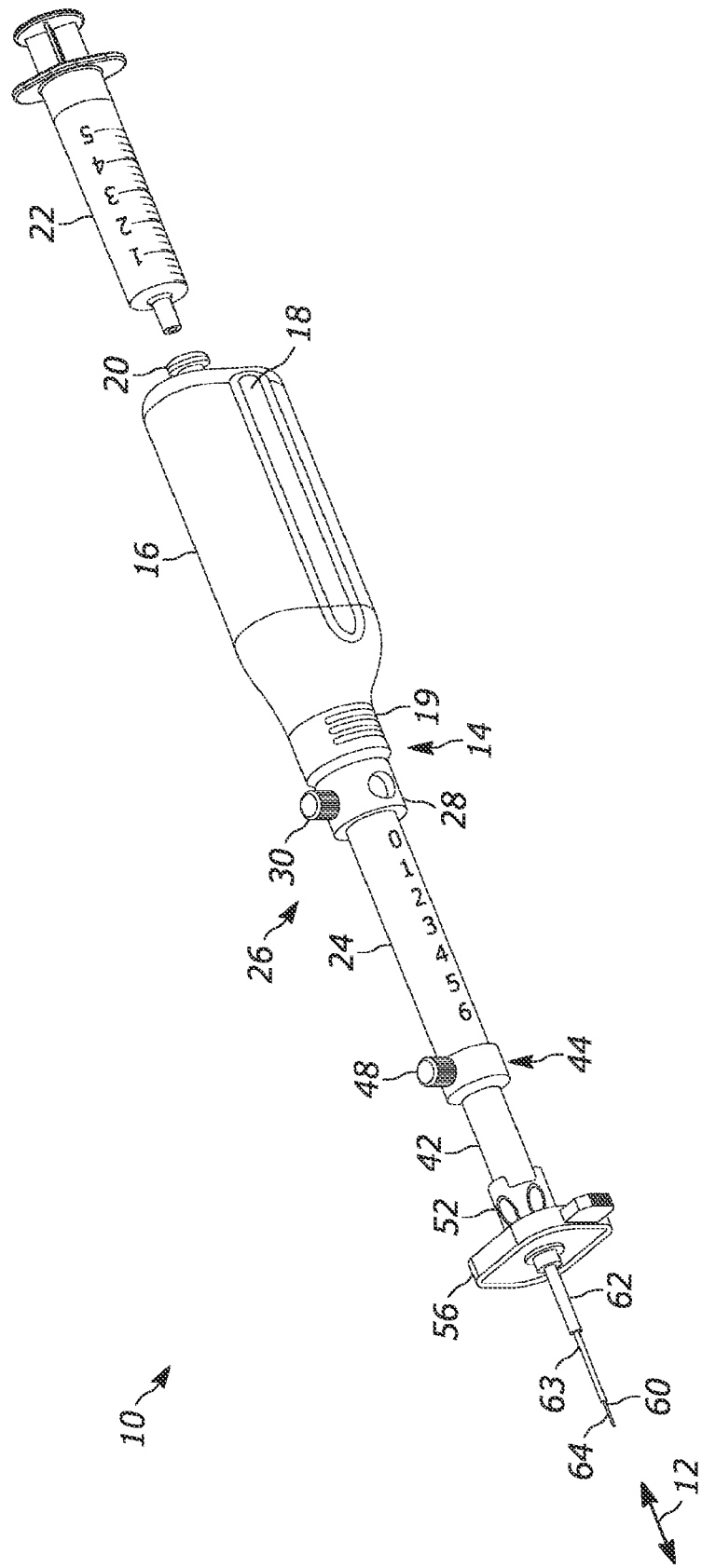
FIG. 1 is a perspective view of a first embodiment of a telescoping tissue harvesting assembly, showing a syringe in an exploded relationship with the assembly.

Referring to FIG. 1, an elongated telescoping assembly 10 is shown which defines a longitudinal axis 12 and which in the example shown can be configured as an endobronchial ultrasound needle (EBUS) assembly. The assembly 10 includes a housing 14 with at least two and in the example shown three segments that are telescopically engaged such that an inner segment nests inside and is slidably engaged with a middle segment which nests inside and is slidably engaged with an outer segment, with the segments having progressively smaller diameters from outer segment to inner segment.

In the example shown, these segments include a hollow handle segment 16 that is the proximal-most segment of the housing 14. The handle segment 16 may be formed in injection-molded plastic, like the remaining segments of the housing 14, and may have an ovular or oval transverse cross-section as shown to aid in gripping. Also, the handle segment 16 may include one or more longitudinally-oriented channel indentations 18 on its outer surface to promote gripping the raised circumferential ridges 19 on the distal portion of the handle segment 16 also to promote gripping. A connector fitting 20 such as a Luer fit may be provided near the proximal end of the housing segment 16 as shown to facilitate connection to external components such as a syringe 22. The fitting 20 may be hollow and may establish the proximal-most segment of a fluid channel that extends coaxially through the housing 14 and that will be described further in reference to FIG. 2.

Figure 6:
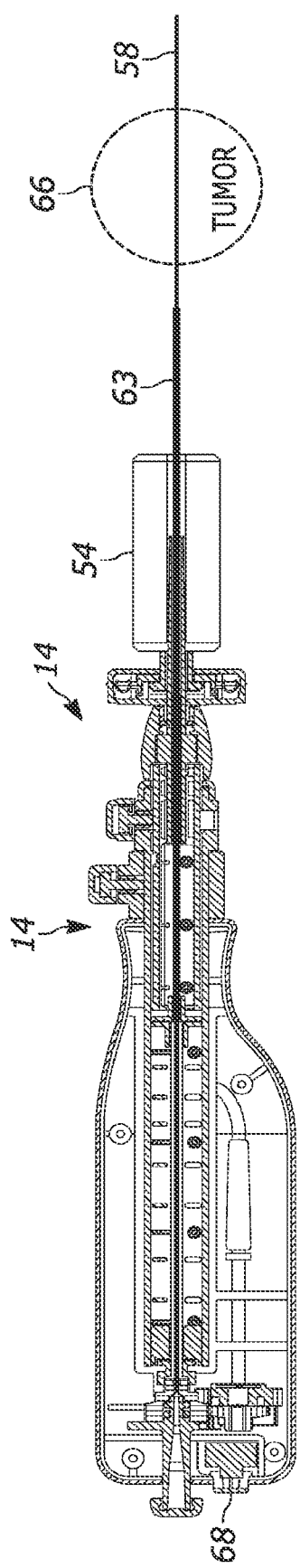
FIGS. 6 and 7 are a side cut-away views of the assembly shown in FIG. 1 in a configuration inside the patient to illustrate the necessity of the needle stop.

Indeed, and now cross-referencing FIGS. 1 and 2, a hollow, generally cylindrical middle segment 24 of the housing 14 extends distally away from the handle segment 16 and is slidably engaged with the handle segment 16 such that the middle segment 24 can telescope within the handle segment 16. To limit axial movement of the middle segment 24 within the handle segment 16, a manipulable mechanical outer stop 26 may be provided. In the example shown the outer stop 26 includes a cylindrical collar 28 that closely surrounds the middle segment 24 and a thumbscrew 30 extending transversely into the collar 28 and threadedly engaged therewith such that the thumbscrew 30 can be tightened against the middle segment 24 to hold the middle segment 24 stationary relative to the collar 28. The collar 28 in turn may be slidably engaged with the middle segment 24. When the stop 26 is set in the most distal position, the handle segment 16 is free to slide back and forth over the length of the middle segment 24. On the other hand, when the stop 26 is set in the most proximal position, the handle segment 16 cannot slide at all. As discussed further below, prior to inserting the needle, the user estimates the distance from the end of the sheath to the distal side of the tumor. The user then sets the stop 26 an appropriate length (the distance previously estimated) away from the distal end of the handle segment 16, tightening the thumbscrew at that position. This is done to limit the "throw" of the needle and prevent it from passing completely through the tumor as otherwise might occur as shown in FIG. 6 and mentioned further below.

The diameter of the middle segment 24 is marginally smaller than the diameter of a segment receiving void 32 formed coaxially in the handle segment 16 such that the middle segment 24 can reciprocate under hand pressure within the void 32.

Note that a central tube 34 forming a proximal portion 36 of the above-alluded to fluid channel can be provided in the handle segment 16 and received in or communicate with a central channel 38 of the middle segment 24, which central channel 38 also forms part of the above-mentioned fluid channel. The tube 34 prevents kinking of the needle within the void 32. In some embodiments the tube 34 may be omitted. The needle of the assembly, described further below, is coupled to a drive assembly 40 in the handle segment 16 through the proximal portion 36 of the fluid channel to impart oscillating rotational motion of the needle.

A hollow, generally cylindrical inner segment 42 of the housing 14 extends distally away from the middle segment 24 and is slidably engaged with the middle segment 24 such that the inner segment 42 can telescope within the middle segment 24. To prevent axial movement of the inner segment 42 within the middle segment 24, a manipulable mechanical inner stop 44 may be provided. In the example shown in FIG. 2, the inner stop 44 includes a cylindrical collar 46 that closely surrounds the inner segment 42 and a thumbscrew 48 extending transversely into the collar 42 and threadedly engaged therewith such that the thumbscrew 48 can be tightened against the inner segment 42 to hold the inner segment 42 stationary relative to the collar 46. The collar 46 in turn may be made integrally with or adhered to by solvent bonding, rf sealing, or other technique to the middle segment 24. The diameter of the inner segment 42 is marginally smaller than the diameter of a segment receiving void 50 formed coaxially in the middle segment 24 such that the inner segment 42 can reciprocate under hand pressure within the void 50 when the thumbscrew 48 is not tightened against the inner segment 42.

A hollow coupling 52 is attached to or formed integrally on the distal end of the inner segment 42 to couple the housing 14 with an endoscope 54. The coupling 52 may be formed, e.g., with interior Luer threads that can directly engage a Luer fitting on the endoscope 54 or that can engage an adapter 56 that in turn is configured to engage the endoscope 54 that does not have a Luer-like connector. An example adapter 56 is shown in FIGS. 13-16 and described further below.

At least one hollow needle 58 having one or more hollow needle segments is supported by the housing 14. The needle 58 extends from a distal cutting tip 60 through the inner, middle, and handle segments 42, 24, 16 to the drive assembly 40, which as further disclosed below includes at least one motor with an output shaft geared to the needle 58. When the housing 14 is coupled to the endoscope 54, the needle 58 extends through the working channel of the endoscope. A coupler tube 62 can extend distally beyond the distal segment 42 as shown and is effectively an extension of the distal segment 42 that provides structural integrity between the distal segment 42, the Luer connector 52, the adapter 56 (if applicable), and the endoscope.

Figure 17:
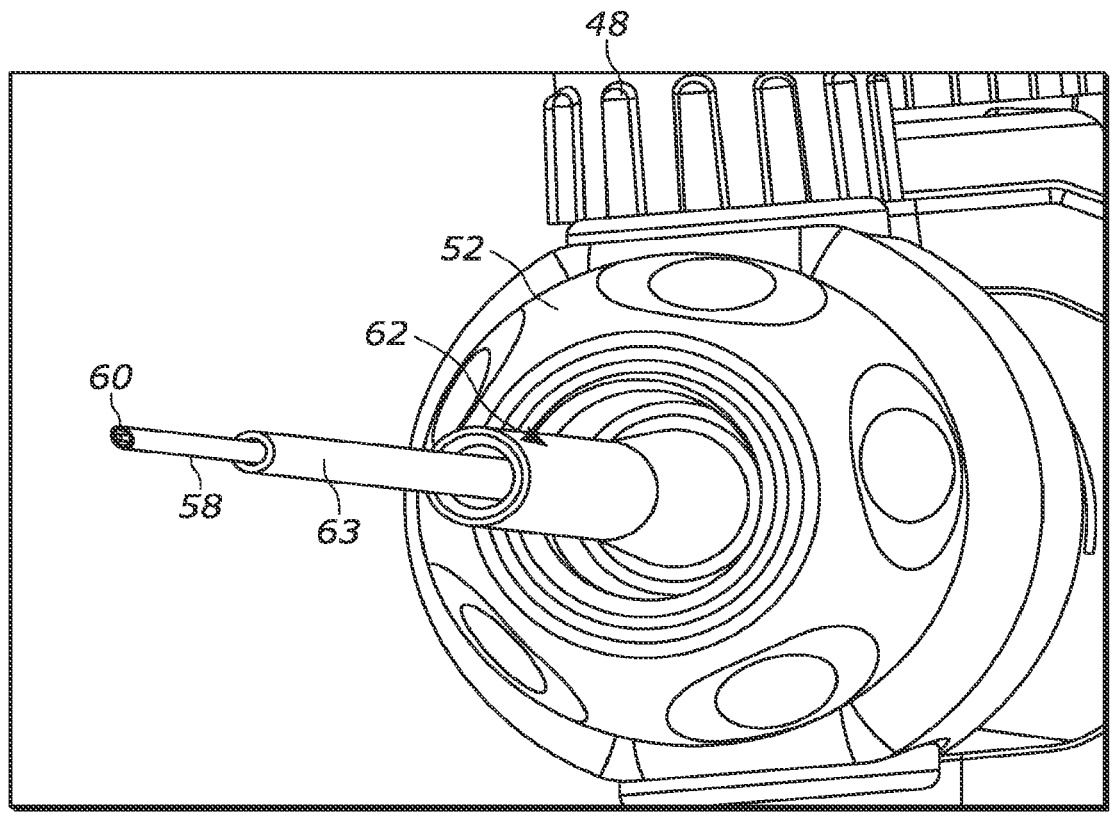
FIG. 17 is an isometric view of the distal portion of the assembly shown in FIG. 1.
Figure 18:
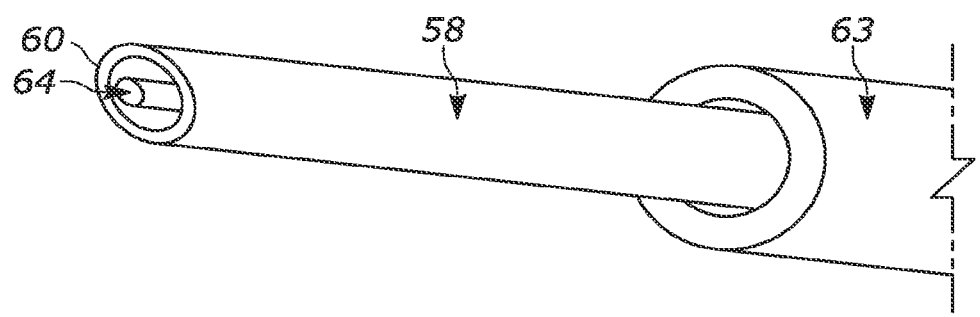
FIG. 18 is a detail view of the distal needle components of FIG. 17.

The interior channel of the hollow needle 58 forms all or part of the above-mentioned fluid channel. Refer briefly to FIGS. 17 and 18. A sheath 63 closely surrounds the needle 58, and a stylet 64 (FIG. 18) can extend through the fluid channel and out of the distal end 60 of the needle for sliding in and out of the needle as needed, e.g., to impede epithelial tissue from entering the needle prior to biopsy of tumor tissue.

Figure 4:
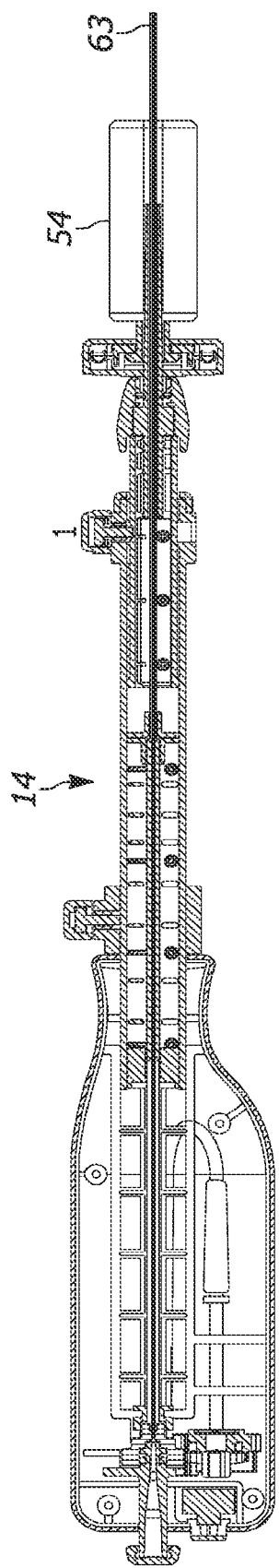

In FIG. 2, the housing 14 is engaged with the endoscope 54 prior to advancing the endoscope into an object such as a patient's body. The inner segment 42 has been moved relative to the middle segment 24 such that the tip of the needle and the distal portions of the sheath 62 and stylet 64 extend marginally out of the distal end of the working channel of the endoscope, and then the mechanical stop 44 manipulated to lock the housing segments axially to prevent further telescoping movement. FIG. 2 shows the initial, fully-extended configuration; FIGS. 3 and 4 show the device after the distal segment 42 has been moved relative to the middle segment 24.

When this configuration of the housing 14 has been established, the housing 14 is disconnected from the endoscope and the endoscope then advanced into the patient. The housing 14 then may be re-connected to the endoscope in the configuration shown in FIG. 4.

Figure 5:
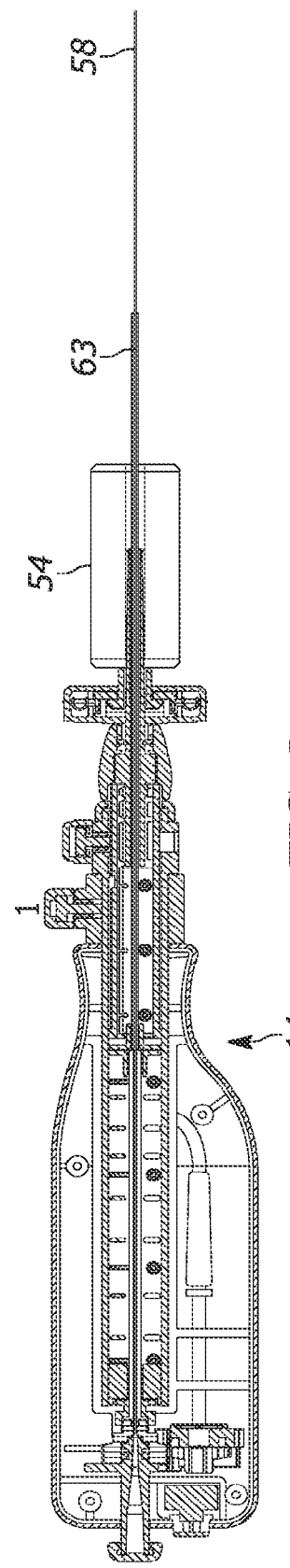
FIG. 5 is a side cut-away view of the assembly shown in FIG. 1 in a shortened configuration to project the needle distally beyond the endoscope.
Figure 7:
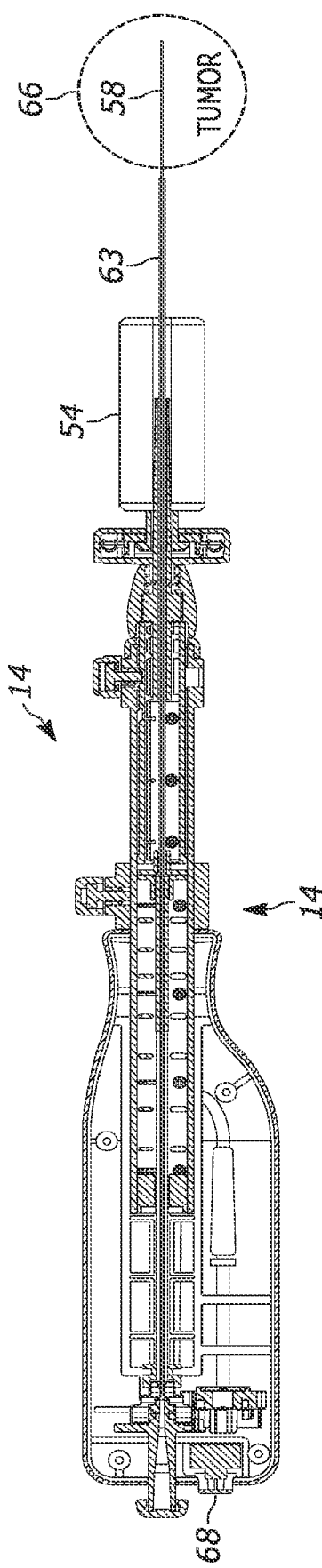
Figure 8:
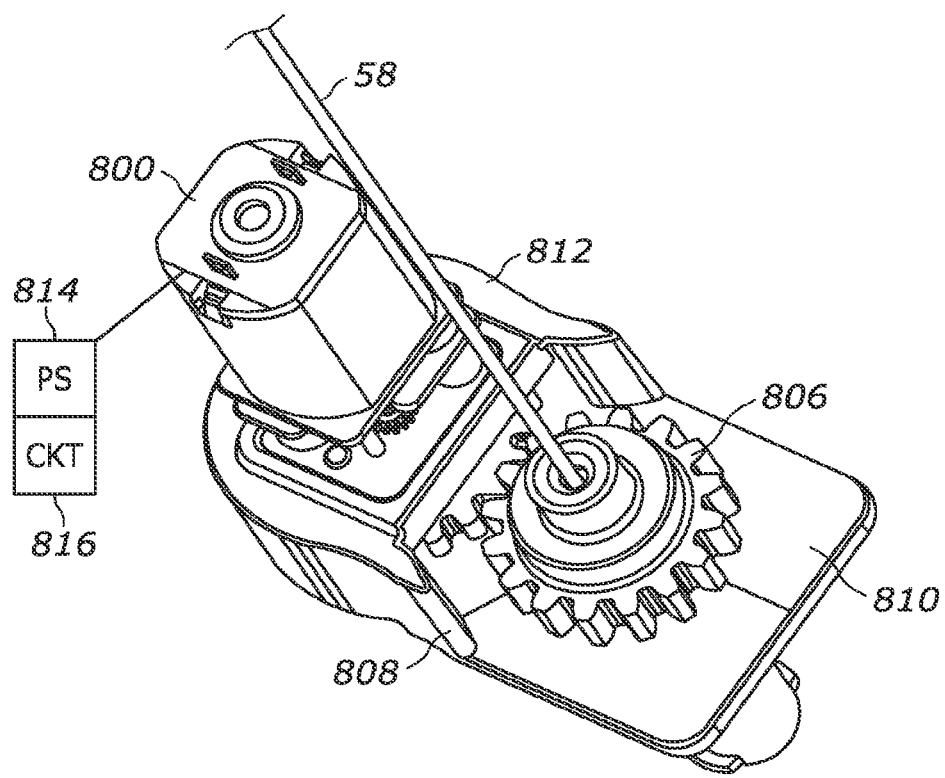
FIGS. 8 and 9 are isometric views from two different perspectives of the motor, gear, and needle subassembly.
Figure 9:
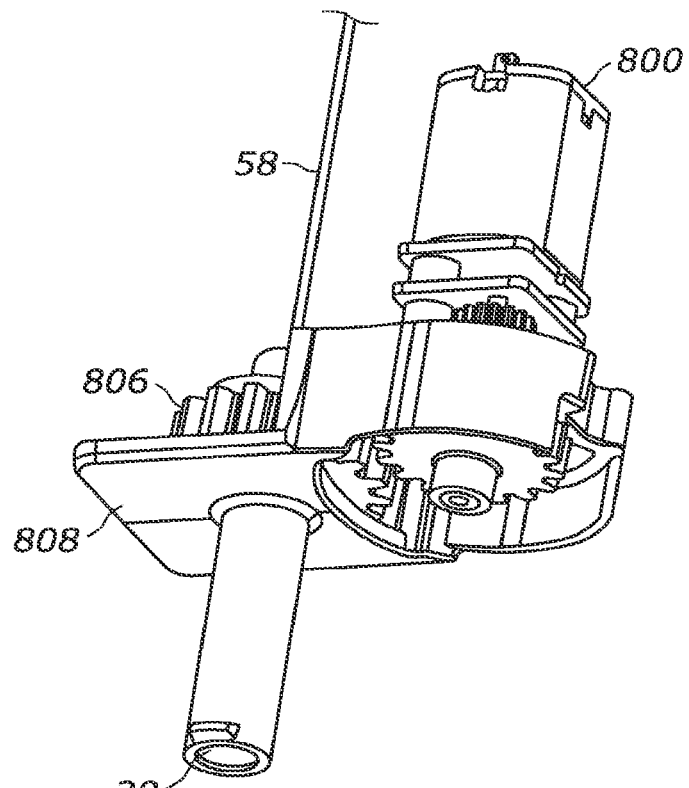
Figure 10:
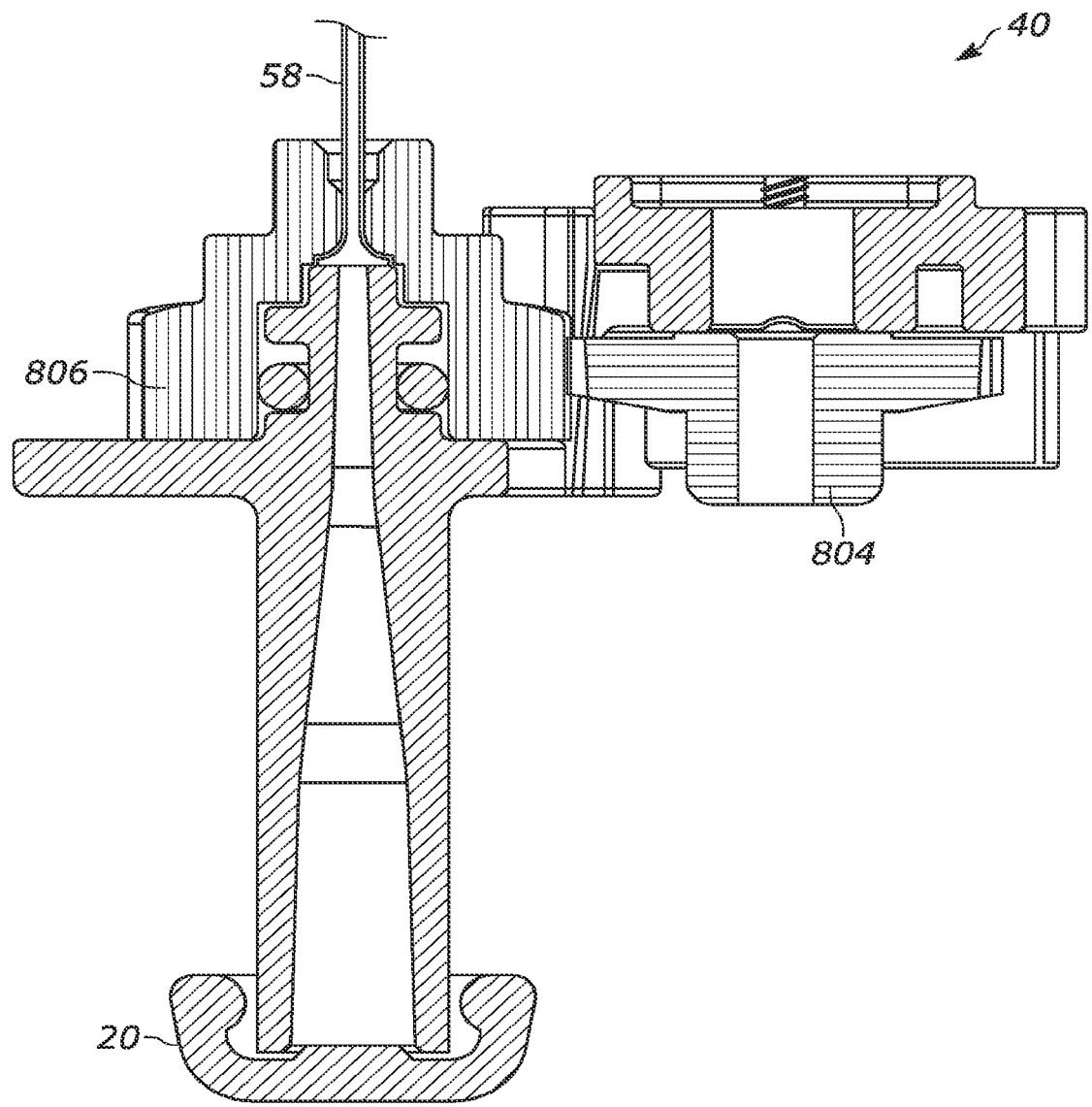
FIG. 10 is a side cut-away view of the subassembly shown in FIGS. 8 and 9.

FIGS. 5-7 illustrate that subsequently, a shorter configuration of the housing 14 can be established by unlocking the proximal stop 26 and moving the handle and middle segments 16, 24 relative to each other to cause the needle 58 to protrude further distally away from the distal end of the endoscope 54 and the distal end of the needle 58 out of the distal end of the sheath 62. The stop 26 can be manipulated to limit the position of the needle relative to the endoscope to avoid over-extending the needle into the patient. In this way, the needle 58 can penetrate tissue 66 (FIG. 7) such as a tumor to be sampled without unintentionally overextending the needle (FIG. 6). The drive assembly 40 can be actuated by manipulating an actuator such as button 68 (FIGS. 2 and 7) on the housing 14 to energize, via a control circuit, a motor to cause the output shaft of the motor to oscillate. As disclosed further below, the output shaft is geared to the needle to cause the needle to rotate in one direction or oscillate in two directions (alternating between clockwise and counterclockwise) in the tissue 66, drawing portions of the tissue in the needle. The syringe 22 shown in FIG. 1 can be engaged with the housing 14 to evacuate the interior of the needle to harvest the tissue for analysis.

Figure 11:
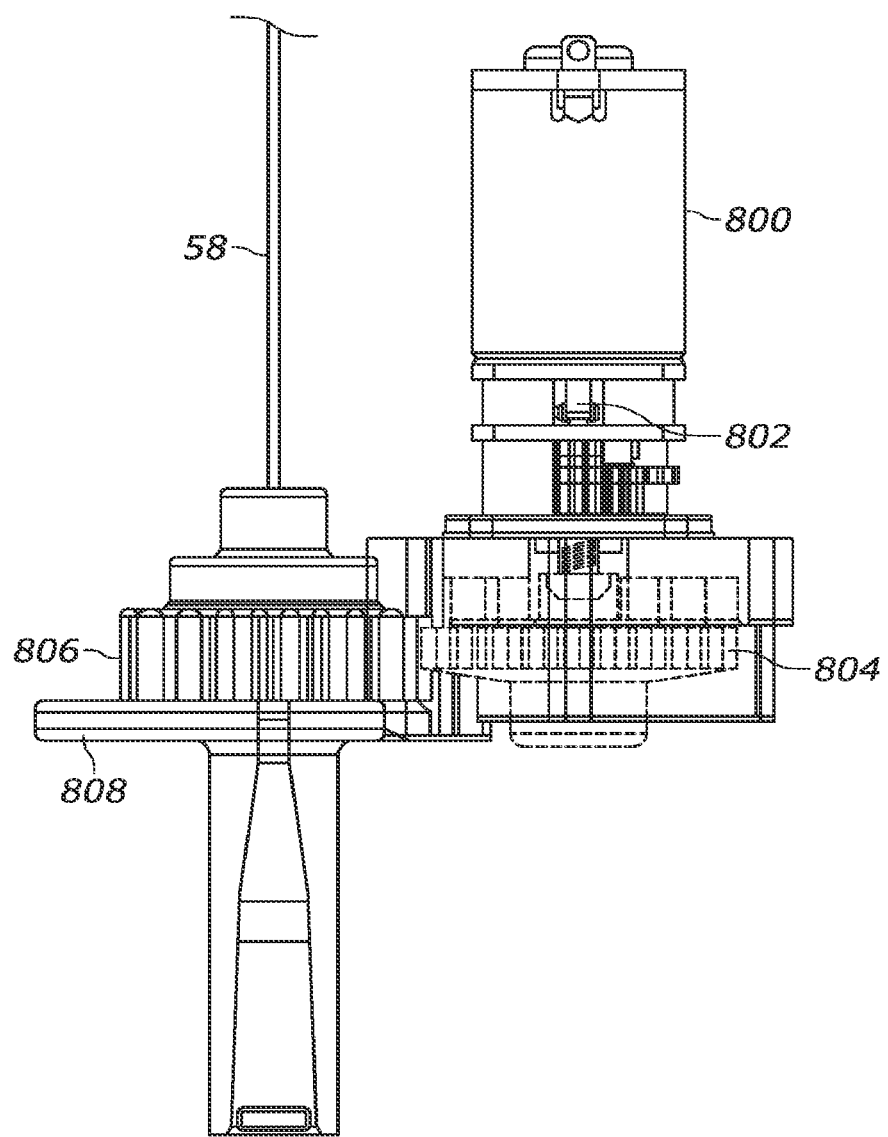
FIG. 11 is a side view, partially transparent, of the subassembly shown in FIGS. 8 and 9.

FIGS. 8-11 illustrate that an example embodiment of the drive assembly 40 in the handle segment 16 may include one or more electric motors 800 (in the example shown, only one motor) coupled to the needle 58 through one or more gears such as but not limited to spur gears. In the example shown and as best illustrated in FIG. 11, an output shaft 802 of the motor 800 is coupled to one or more motor gears 804 that are meshed with one or more needle gears 806, with the needle 58 being bonded to or molded with or otherwise affixed to the needle gears 806 to rotate with the needle gears 806. The gear train may be configured to reduce rotational speed from the speed of rotation of the motor shaft 802 to a slower needle rotation speed.

The motor 800 with gears can be supported on a motor plate assembly 808, which may include two flat plates 810, 812 (FIG. 8) that are parallel to each other and that are staggered in the longitudinal dimension from each other to respectively support the needle gear 806 with needle 58 and the motor 800 with motor gear 804. As shown schematically in FIG. 8, a power supply 814 (such as a battery) is disposed in the housing 14 and is connected to the motor 800 to energize the motor 800.

Also, a control circuit 816 is located in the housing 14 and is coupled to the button 68, so that when the button 68 is manipulated, the control circuit is activated to energize the motor 800 to cause the output shaft 802 of the motor (and, hence, the needle 58) to rotate in a single direction only (i.e., clockwise or counterclockwise) or to oscillate (i.e., to rotate alternatingly between CW and CCW). For oscillation, the control circuit alternatingly reverses the direction of rotation of the motor shaft, from clockwise to counter-clockwise and back again, based on a time period for rotation in one direction or a position of rotation. Any of the control circuits described in the above-referenced U.S. patent may be used for this purpose. Note that for single direction rotation only, no control circuit need be used other than an electrical connection from a battery to the switch that energizes the motor.

Figure 12:
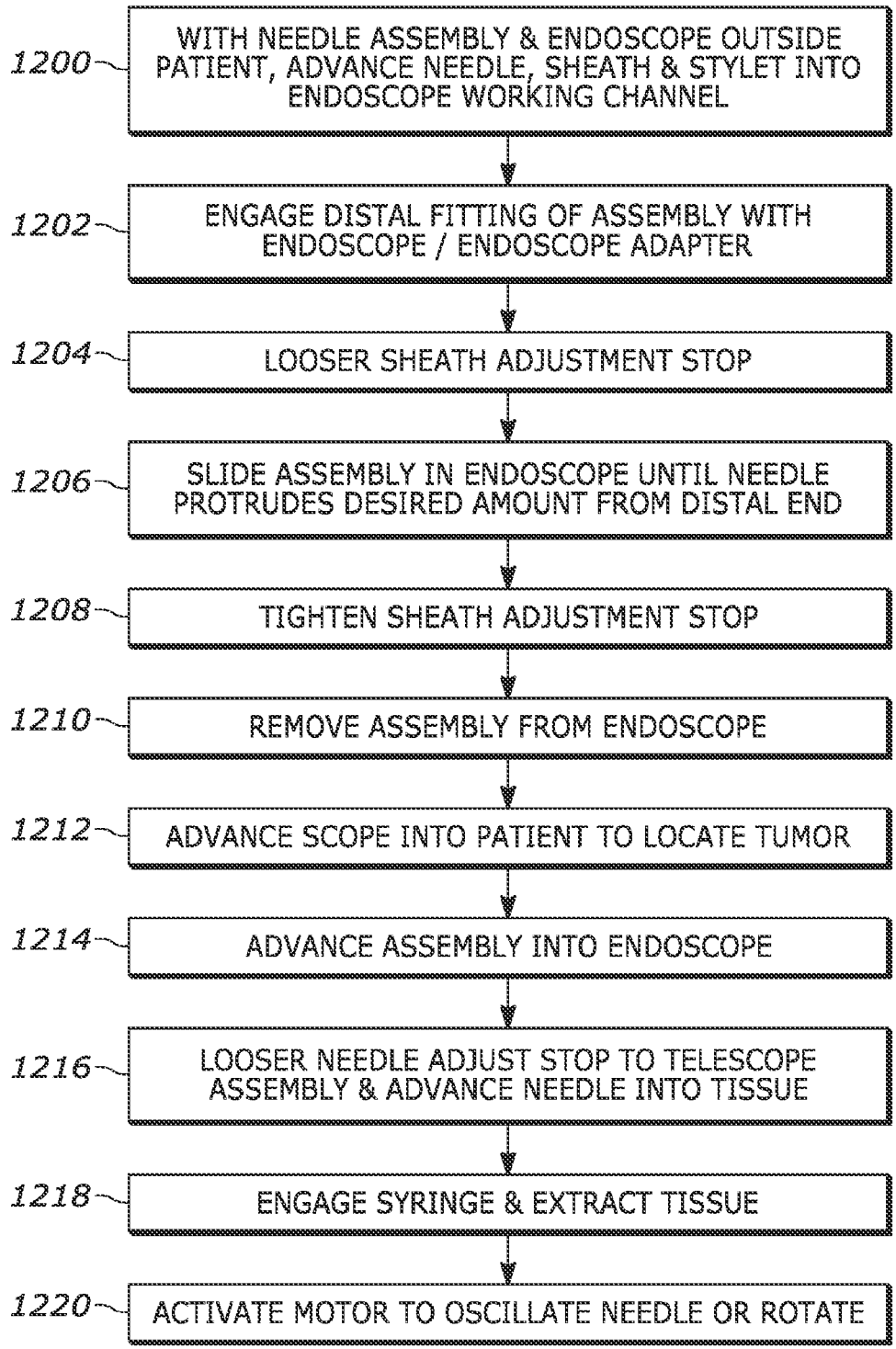
FIG. 12 is a flow chart of the use steps of the assembly shown in FIG. 1.

FIG. 12 illustrates a method of using the assembly 10 shown in FIGS. 1-11 with the endoscope 54. Commencing at block 1200, with the assembly 10 and endoscope outside of the patient, the needle (with sheath and typically stylet) is engaged with the endoscope working channel. At block 1202 the coupling 52 is coupled to the endoscope or, when needed, the adapter 56 which in turn is coupled to the endoscope. Moving to block 1204, the stop 44 is loosened and at block 1206 the assembly 10 is moved until the needle, sheath, and stylet protrude from the distal end of the endoscope by a desired amount. Proceeding to block 1208, the stop is tightened to lock the configuration of the housing 14 of the assembly 10 in place and the assembly 10 removed from the endoscope at block 1210.

When it is desired to harvest tissue from a patient, at block 1212 the endoscope is advanced into the patient under visualization to locate the tissue to be harvested, e.g., a tumor. The assembly 10 is advanced into the endoscope working channel at block 1214 so that the needle, sheath, and stylet protrude (the distance set in step 1206) beyond the distal tip of the endoscope, at which point the stop 26 can be loosened at block 1216 to telescope the housing 14 as needed to advance the needle into the tissue. Once the needle 58 is in the tumor, the stylet 64 is removed and the syringe 22 is attached to the fluid channel previously occupied by the stylet. Suction is applied by the syringe at block 1218, and then the motor is activated at block 1220 by manipulating the button 68 to rotate or oscillate the needle within the needle to harvest tissue, which can be evacuated at block 1220.

Figure 13:
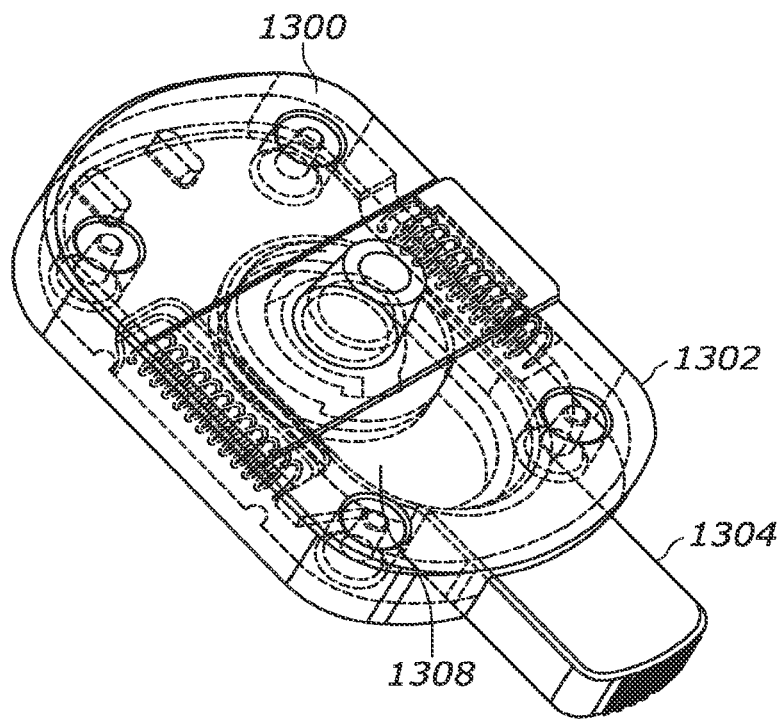
FIG. 13 is a partially transparent perspective view of an example assembly-to-endoscope adapter.
Figure 14:
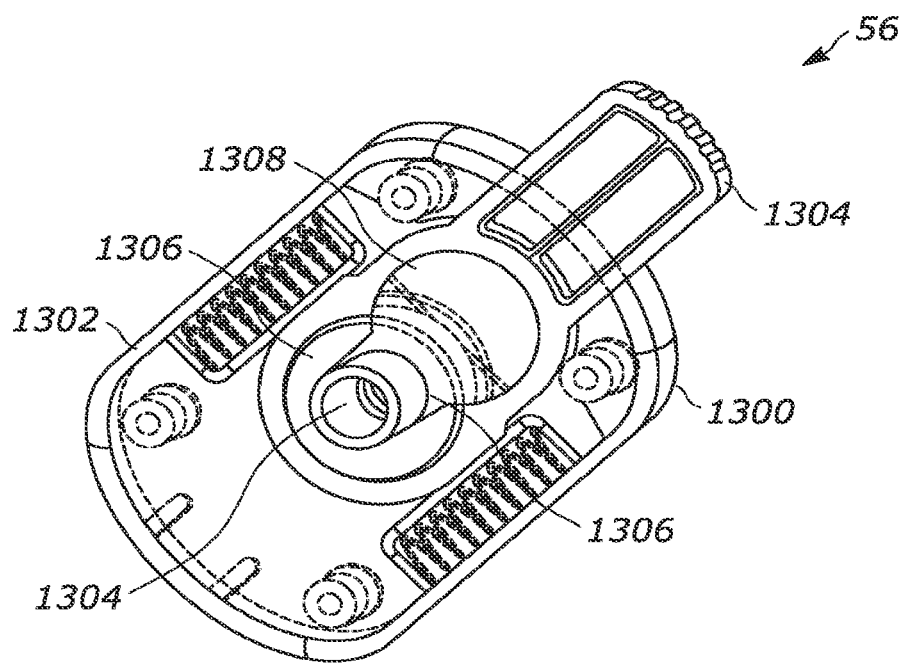
FIG. 14 is a bottom partially transparent view of the adapter shown in FIG. 13.
Figure 15:
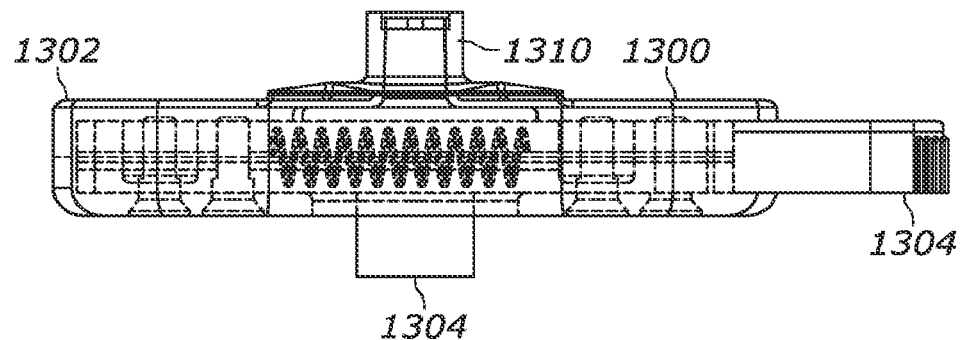
FIG. 15 is a side partially transparent view of the adapter shown in FIG. 13.

As understood herein, some endoscopes have fittings that can be engaged with the coupling 52 shown in FIG. 1. Other endoscopes may have couplings such as the mushroom-shaped hollow coupling 1600 shown in FIG. 16 that cannot engage the coupling 52 of the needle assembly, in which case the adapter 56 is provided. FIGS. 13-15 illustrate an example adapter 56.

Figure 16:
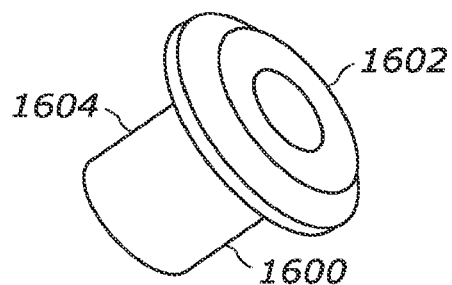
FIG. 16 is an isometric view of the working channel collar of an example endoscope.

The adapter 56 includes a flat hollow body 1302 with a hollow receptacle 1304 through which the head 1602 of the coupling 1600 of the endoscope 54 in FIG. 16 can be received. As shown, the head 1602 has a larger diameter than a stalk 1604 of the coupling 1600 and the head 1602 may have a beveled outer edge, giving the endoscope coupling 1600 a somewhat mushroom-shaped appearance.

A slide 1304 is slidably disposed in the body 1302 of the adapter 1300. The slide 1302 is formed with a small opening 1306 and a large opening 1308, with a passageway between the openings. The small opening 1306 and passageway to the large opening is smaller than the diameter of the head 1602 of the coupling 1600 of the endoscope, whereas the large opening 1308 has a diameter larger than the diameter of the head 1602.

The slide 1304 may be spring-loaded into the configuration shown in FIGS. 13 and 14, in which the small opening 1306 is substantially aligned (coaxially) with the receptacle 1304. The slide 1304 can be pushed inwardly toward the body 1302 of the adapter 1300 against spring pressure to align the large opening 1308 coaxially with the receptacle 1304, allowing the head 1602 to be advanced through the receptacle 1304 and large opening 1308. The slide may then be released to cause it to move outward as the passageway between the openings 1306, 1308 rides past the stalk 1604 of the coupling 1600 until the small opening 1306 is once again aligned with the receptacle 1304, trapping the head 1602 of the coupling within the adapter 1300 to thereby engage the adapter with the coupling 1600. Opposite the receptacle 1304, the adapter 1300 is formed with a fitting 1310 such as a Luer fitting configured to engage the coupling 52 of the needle assembly 10, thereby coupling the needle assembly 10 with the endoscope 54. Both the fitting 1310, body 1302, and receptacle 1304 of the adapter 1300, as well as the coupling 1600 of the endoscope, are hollow such that the needle 58 (and coupler tube 62, sheath 63, and stylet 64) can extend completely through the coupling structure. To decouple the endoscope 54 from the needle assembly 10, the slide 1304 is once again squeezed inwardly to align the large opening 1308 with the receptacle 1403, allowing the head 1602 of the endoscope coupling to be withdrawn from the adapter 1300.

Accordingly, an adapter for connecting a needle assembly to an endoscope includes one or more of the following components: a body formed with a hollow receptacle through which a head of an endoscope coupling of the endoscope can be received. The head has a larger diameter than a stalk of the endoscope coupling. A slide is slidably disposed in the body and is formed with a small opening, a large opening, and a passageway between the openings. The diameter of the small opening and the diameter of the passageway are smaller than the diameter of the head and larger than the diameter of the stalk, whereas the diameter of the large opening is diameter larger than the diameter of the head. The slide is movable from a first configuration, in which the small opening is substantially aligned (coaxially) with the receptacle, and a second configuration, in which the large opening is aligned coaxially with the receptacle, allowing the head to be advanced through the receptacle and large opening. The slide may then be moved back to the first configuration, trapping the head of the coupling within the adapter.

While the particular device is herein shown and described in detail, it is to be understood that the subject matter which is encompassed by the present invention is limited only by the claims.

Components included in one embodiment can be used in other embodiments in any appropriate combination. For example, any of the various components described herein and/or depicted in the Figures may be combined, interchanged, or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An endobronchial ultrasound needle (EBUS) assembly, comprising:
    a housing with a handle section and at least a first segment and a second segment coupled telescopically, wherein the first segment is distally located from the handle section and the second segment is distally located from the first segment;
    the first segment configured to telescope relative to the handle section and the second segment configured to telescope relative to the first segment;
    at least one hollow needle supported by the housing;
    wherein the first segment and the second segment are each configured such that telescopically adjusting the first segment and the second segment alters a length of protrusion of the hollow needle distally beyond the housing;
    at least one motor in the handle section, the motor geared to the needle, the motor configured to cause the needle to rotate relative to the handle section, the motor secured to a motor mount, and a proximal end of the needle rotatably secured adjacent to the motor mount;
    a luer fitting passing through the motor mount, the luer fitting configured to rotatably connect to the proximal end of the needle thereby allowing the needle to rotate without rotating the luer fitting while establishing a fluid channel between the luer fitting and the needle, wherein a proximal end of the luer fitting extends externally from a proximal end of the handle to engage a syringe;
    an endoscope adapter located proximate a distal end of the needle, the endoscope adapter configured to engage a mushroom-shaped endoscope coupling comprised of a smaller diameter distal end and a larger diameter proximal end, the endoscope adapter further including:
    an outer body with a passageway extending therethrough, wherein the passageway is sized to permit passage of the endoscope coupling;
    a spring-loaded slide mechanism having a pair of openings including a smaller opening and a larger opening with an open area between the pair of openings,
    wherein the smaller opening is smaller than the proximal end of the endoscope coupling, but larger than the distal end of the endoscope coupling and the larger opening is larger than the proximal end of the endoscope coupling;
    whereby the spring loaded slide mechanism is configured such that the spring loaded slide mechanism is biased to maintain the smaller opening in axial alignment with a central longitudinal axis of the needle to secure the endoscope coupling to the needle while permitting rotation of the needle relative to the endoscope coupling.

2. The EBUS assembly of claim 1, comprising a sheath surrounding the needle.

3. The EBUS assembly of claim 1, wherein the housing comprises at least a third segment coupled telescopically with the second segment.

4. The EBUS assembly of claim 1, comprising a power supply in the housing connected to the motor to energize the motor.

5. The EBUS assembly of claim 1, comprising a manipulatable actuator on the housing to energize the motor.

6. The EBUS assembly of claim 1, comprising a first manipulatable mechanical stop on the housing, the first manipulatable mechanical stop configured to move from a first position, in which the first segment and the second segment can telescope relative to each other, to a second position, in which the first segment and the second segment cannot telescope relative to each other.

7. The EBUS assembly of claim 6, wherein the first manipulatable mechanical stop comprises a thumb screw.

8. The EBUS assembly of claim 6, comprising a second manipulatable mechanical stop on the housing, the second manipulatable mechanical stop configured to move to lock the second segment to a third segment.

9. The EBUS assembly of claim 1, wherein the motor is controlled by a circuit to cause the needle to oscillate.

10. A telescoping assembly, comprising:
    a housing with a handle section and at least a first segment and a second segment coupled telescopically, wherein the first segment is distally located from the handle section and the second segment is distally located from the first segment;
    the first segment configured to telescope relative to the handle section and the second segment configured to telescope relative to the first segment;
    at least one hollow needle supported by the housing;
    wherein the first segment and the second segment are each configured such that telescopically adjusting the first segment and the second segment alters a length of protrusion of the hollow needle distally beyond the housing;
    at least one motor in the handle section, the motor having an output shaft geared to the needle, wherein the at least one motor is configured to cause rotation of the needle relative to the handle section;
    the motor secured to a motor mount, and a proximal end of the needle rotatably secured adjacent to the motor mount;
    a luer fitting passing through the motor mount, the luer fitting configured to rotatably connect to the proximal end of the needle thereby allowing the needle to rotate without rotating the luer fitting while establishing a fluid channel between the luer fitting and the needle, wherein a proximal end of the luer fitting extends externally from a proximal end of the handle to engage a syringe;
    an endoscope adapter located proximate a distal end of the needle, the endoscope adapter configured to engage a mushroom-shaped endoscope coupling comprised of a smaller diameter distal end and a larger diameter proximal end, the endoscope adapter further including:
    an outer body with a passageway extending therethrough, wherein the passageway is sized to permit passage of the endoscope coupling;
    a spring-loaded slide mechanism having a pair of openings including a smaller opening and a larger opening with an open area between the pair of openings,
    wherein the smaller opening is smaller than the proximal end of the endoscope coupling, but larger than the distal end of the endoscope coupling and the larger opening is larger than the proximal end of the endoscope coupling;
    whereby the spring loaded slide mechanism is biased to maintain the smaller opening in axial alignment with a central longitudinal axis of the needle to secure the endoscope coupling to the needle while permitting rotation of the needle relative to the endoscope coupling;
    and at least one control circuit to energize the motor to cause the output shaft of the motor to oscillate alternatingly clockwise (CW) and counterclockwise (CCW) or to rotate only in one direction, CW or CCW.

11. The assembly of claim 10, comprising a sheath surrounding the needle.

12. The assembly of claim 10, wherein the housing comprises at least three segments coupled telescopically and configured as an endobronchial ultrasound needle (EBUS) assembly.

13. The assembly of claim 10, comprising a power supply in the handle section connected to the motor to energize the motor.

14. The assembly of claim 10, comprising a manipulatable actuator on the housing to energize the motor.

15. The assembly of claim 10, comprising a stylet in the needle, the stylet configured to move within the needle to impede epithelial tissue from entering the needle prior to biopsy of tumor tissue.

16. The assembly of claim 10, comprising an endoscope slidably engaged with the needle.

* * * * *